US010105115B2

(12) United States Patent
McCabe et al.

(10) Patent No.: US 10,105,115 B2
(45) Date of Patent: Oct. 23, 2018

(54) METHOD AND SYSTEM FOR PROCESSING MEDICAL IMAGE DATASETS

(75) Inventors: David McCabe, Swindon (GB); Timor Kadir, Oxford (GB); Eduardo Rodrigues, Oxford (GB)

(73) Assignee: Mirada Medical Limited, Oxford (GB)

( * ) Notice: Subject to any disclaimer, the term of this patent is extended or adjusted under 35 U.S.C. 154(b) by 336 days.

(21) Appl. No.: 13/304,512

(22) Filed: Nov. 25, 2011

(65) Prior Publication Data

US 2013/0135287 A1    May 30, 2013

(51) Int. Cl.
*A61B 6/00* (2006.01)
*A61B 6/03* (2006.01)

(52) U.S. Cl.
CPC ............ *A61B 6/463* (2013.01); *A61B 6/466* (2013.01); *A61B 6/5223* (2013.01); *A61B 6/5235* (2013.01); *A61B 6/5247* (2013.01); *A61B 6/032* (2013.01); *A61B 6/037* (2013.01)

(58) Field of Classification Search
USPC .......... 345/419; 382/154, 285; 715/868–852
See application file for complete search history.

(56) References Cited

U.S. PATENT DOCUMENTS

| | | | | |
|---|---|---|---|---|
| 6,765,566 | B1* | 7/2004 | Tsao .............................. | 345/419 |
| 7,822,254 | B2* | 10/2010 | Yatziv et al. ................. | 382/131 |
| 2005/0110788 | A1* | 5/2005 | Turner et al. ................. | 345/419 |
| 2010/0266174 | A1* | 10/2010 | Lobregt et al. ............... | 382/128 |

OTHER PUBLICATIONS

Raine-Fenning et al. (The reproducibility of endometrial volume acquisition and measurement with VOCAL-imaging program, Ultrasound Obstet Gynecol 2002).*
G. L. Sannazzari, R. Ragona, M.G. Redda, F.R. Giglioli, G. Isolato and A. Guarneri, CT-MRI image fusion for delineation of volumes in three-dimensional conformal radiation therapy in the treatment of localized prostate cancer, British Journal of Radiology, 2002, 5 pages.
D. Hill, P. Batchelor, M. Holden and D. Hawkes, "Medical image registration", Institute of Physics Journal, 45 pages.
Jun. 3, 2014 Office Action of counterpart European Patent Application No. 12 194 063.9-1660, issued by the European Patent Office.
Jan. 15, 2015 Office Action of counterpart EP Application No. 12 194 063.9 issued by the European Patent Office.

(Continued)

*Primary Examiner* — Kyle Zhai
(74) *Attorney, Agent, or Firm* — Optimus Patents US, LLC

(57) ABSTRACT

A method and system are provided for creating and simultaneously displaying medical scan images, from each of first (780) and second (530) medical scan datasets, obtained by scanning a 3-dimensional (3-D) object with different scanning modalities. A first image (410) is derived from the first (780) dataset, the first image (410) lying in a first plane corresponding to an acquisition plane of the first (780) dataset. A second image (420) is obtained from the second dataset (530), the second image also lying in the first plane. The second image may be obtained by re-slicing the second data set. One or both medical scan datasets may be multi-volume datasets. The invention may improve viewing resolution and/or speed, when viewing a multi-series MRI scan together with a CT and/or a PET scan.

16 Claims, 10 Drawing Sheets

(56) References Cited

OTHER PUBLICATIONS

Congenital Tarsal Coalition: Multimodality Evaluation with Emphasis on CT and MR Imaging; Newman et al.; RG vol. 20; No. 2; Mar.-Apr. 2000; pp. 321-332.
Isochronous Assessment of Cardiac metabolism and Function in Mice Using Hybrid PET/MRI; Buscher et al.; The Journal of Nuclear Medicine; vol. 51, No. 8; Aug. 2001; pp. 1277-1284.

* cited by examiner

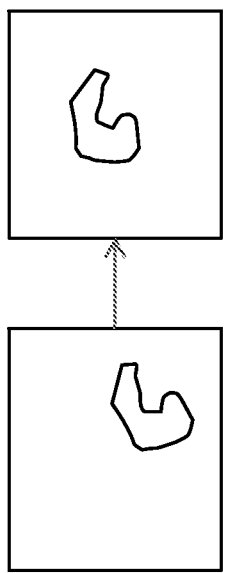

Figure 1: Rigid alignment

In 3D 6 parameters require calculation:
Translations (3 parameters)
Rotation (3 parameters)

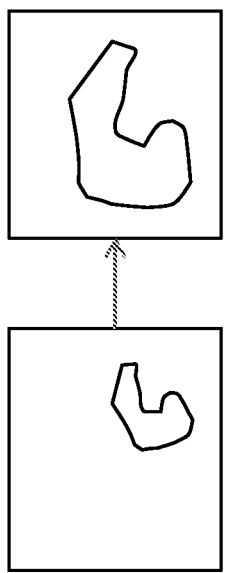

Figure 2: Affine alignment

In 3D 12 parameters are required:
Translations (3 parameters)
Rotation, Shearing and Scale (9 parameters)

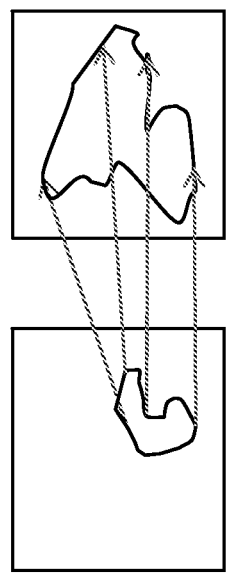

Figure 3: Deformable alignment

In 3D 3 parameters are required per image element:
Translations (3 parameters) at each image location
This can be thousands of parameters for a 3D image MRI images:                    CT images:
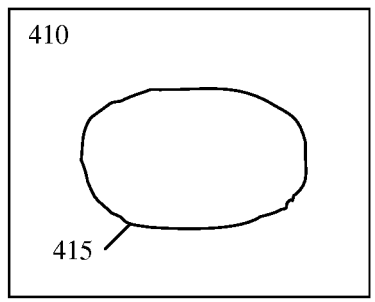
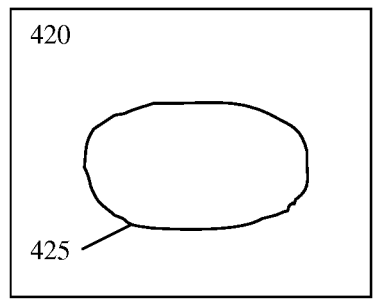
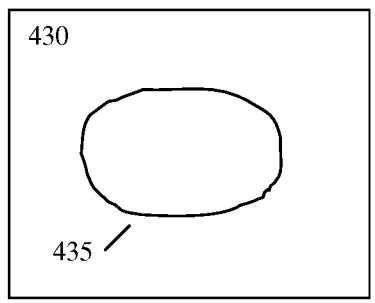
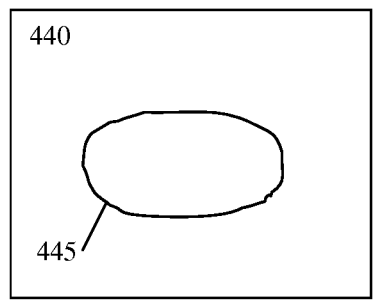
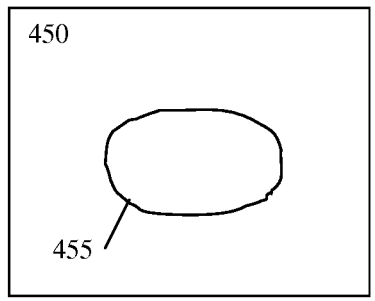
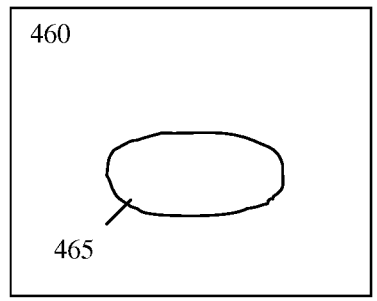
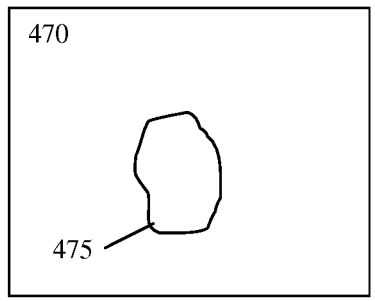
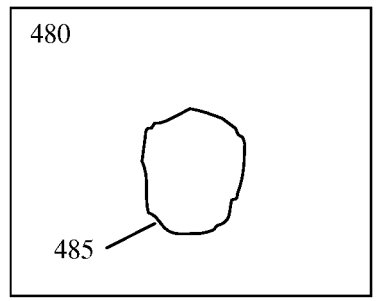
Fig. 4

| 3-D dataset type | Volume | Number of 2-D slices in each volume | Part of Object scanned | Orientation of acquisition; timing |
|---|---|---|---|---|
| 1. MRI multiseries | First volume: shows first series | 100 | Head | Axial: Normal to acquisition plane lies along the long axis of body |
| | Second volume: shows second series | 80 | Head | Coronal |
| | Third volume: shows third series | 50 | Head | Saggital |
| 2. CT | First volume: Shows first phase | 1000 | Head | Axial |
| | Second volume: Shows second phase | 1000 | Head | Axial; five seconds after first phase of CT scan |
| 3. PET | Only one volume | 80 | Head | Axial |

Fig. 8

| 3-D dataset type | Volume | Number of 2-D slices in each volume | Part of Object scanned | Orientation of acquisition |
|---|---|---|---|---|
| 1. MRI multiseries | First volume: shows first series | 100 | Head | Axial |
| | Second volume: shows second series | 80 | Heart | Normal to acquisition plane lies at 90 degrees to long axis of body, and plane is parallel to face 772 of cuboid in fig. 7 |
| | Third volume: shows third series | 30 | Pancreas | Coronal |
| 2. CT | First volume: Shows first phase | 1000 | Whole body | Axial |
| | Second volume: Shows second phase | 1000 | Whole body | Axial |
| 3. PET | Only one volume | 80 | Head | Axial |

Fig. 9

METHOD AND SYSTEM FOR PROCESSING MEDICAL IMAGE DATASETS

TECHNICAL FIELD

The present invention concerns the processing of datasets obtained during medical scans.

BACKGROUND ART

A variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an imaging modality.

Typically, a medical scan provides a 'dataset'. The dataset comprises digital information about the value of a variable at each of many points. The points are different spatial locations that are spread throughout 3 physical dimensions, i.e. each point is at a particular location on a three dimensional grid. The variable may typically be an intensity measurement. The intensity may be, for example, an indication of the X-Ray attenuation of the tissue at each particular point.

In such a three dimensional dataset, the element of the scan image located at a particular spatial location may be referred to as a 'voxel'. A voxel is therefore analogous to a 'pixel' of a conventional 2-Dimensional image.

Although the dataset of the medical scan is 3-Dimensional, it is typically displayed to a user as a two dimensional image on a medical imaging workstation. An image slice from a 3-d dataset is simply a 2-d representation, consisting of those data points that lie on a particular 2-d plane through the 3-d image. A typical 3-d dataset, such as one from an MRI scan, will have a matrix of regularly spaced data points. As a non-limiting example, the MRI-scan may have data points whose centres are spaced by 1 millimeter in the x- and y-directions across any plane of the scan. Consecutive planes may, for example, be parallel and separated by 7 millimeters.

The 3-D scan may therefore be divided up into tens or hundreds of parallel 2-D images, for display purposes. The user of a workstation can then flick through the images in sequence, for example, thereby allowing a view of successive cross sections of the tissue that was scanned.

Typical workstations allow the 2-D slices to be viewed individually, or sequentially in successive steps. The view may typically be along a selected one of three perpendicular directions. For a human subject lying down, the axes of the three perpendicular directions may, for example, be along the 'long axis' of the body, 'across' the body from one side to the other, and through the body from top to bottom. These axes are conventionally referred to as:
(i) 'axial', for a cross-section that lies along the long axis of the body;
(ii) 'coronal', for a cross-section that lies along an axis running from the front to back; and
(iii) 'sagittal', for a cross-section that lies along an axis that runs from side to side.

Henceforth, the term 'dataset' should be construed as meaning a three dimensional dataset that results from performing a medical scan. However, when the scan image is displayed, only a two dimensional slice of the dataset may be on view at any one time as an image.

Medical scan images may include information about a wide variety of anatomical features and structures. For example, a scan image may show various types of healthy tissue, such as bone and organs within the body. A scan image may also show abnormal tissues. The purpose of obtaining a medical scan image is often to detect abnormal tissue. So, a typical example of an application of medical imaging is in the identification and 'staging' of cancerous tumours.

'Multiple modalities' may be used to provide medical scan images. This approach involves obtaining scan images of the same region of tissue by more than one modality. For example, the same region of tissue may be imaged using both a PET scan and a CT scan. Scanners that can carry out multiple mode scans are referred to as 'hybrid scanners'. Typically, a hybrid scanner allows the subject to be scanned by both modalities in the same sitting.

The usual prior art approach to images that are not in the same frame of reference is to align the images using a more complex transformation than was needed for images that are in the same frame of reference. This process of aligning images is known as image registration. One aim of image registration may simply to correct for differences in patient position.

There are three well known image registration methods. These are termed 'rigid', 'affine' and 'deformable' registration. FIGS. 1-3 illustrates each of these registration methods:
(i) FIG. 1 shows a rigid alignment method of image registration.
(ii) FIG. 2 shows an affine alignment method of image registration.
(iii) FIG. 3 shows a deformable alignment method of image registration.

There are a number of techniques in the prior art which allow a user to delineate regions using multiple imaging volumes.

One approach presents a first image as a base layer, over which one or more semi-transparent overlays are displayed. This approach is known as a 'fused view' in medical imaging. This approach enables the user to view one image, whilst being able to view and use information from overlying images that are derived from another dataset.

However, various datasets may be acquired at different orientations and resolutions. So either a rigid or non-rigid transformation is usually required to produce each overlay image. As a consequence, the image data shown to the user in the overlay images(s) is not the originally captured image data for that image. The data has been warped or rotated, or in some other way resampled, in order to create the overlay image.

This may be problematic. The resolution of the image shown in the overlay may not produce resampled images of sufficient quality. For example, MR images are typically highly anisotropic, which means that the voxels may not be cuboid. The voxels may typically be 3 mm×0.3 mm×8 mm. Such images are best viewed in their original orientation, and do not produce clear images if rotated or warped. This is a major constraint on known imaging systems.

The present invention therefore relates to display logic and/or image processing steps required to produce convenient displays of multiple images which have been acquired in a set.

Medical image display software typically renders 3D scans as 2D cuts through the 3D volume. A processing step known as 'volume reconstruction' is used to create a 3D volume from the stack of 2D images produced by the scanner. The resulting displays are called 'Multi-Planar Reconstructions' or MPRs for short. For example, it is conventional to show 3D medical images in 3 planes: axial—head to foot slices, coronal—front to back slices and sagittal—left to right slices. Some software provides the user the ability to adjust the orientation of the view. Each view has an orientation, position and extent which determines exactly which part of the 3D image is shown. In some advanced visualisation software it is possible to define views where the orientation is not a plane, but is a curved cut of the 3D volume.

Some of the above medical images may be acquired in groups with little or no patient motion between acquisitions. For example, MR images are very typically acquired using:
(i) multiple pulse sequences, to generate different image appearance;
(ii) gated image sequences, where images acquired for different points of the breathing or cardiac cycle;
(iii) dynamic sequences, where the uptake of an image contrast agent is observed using multiple images.

Similarly, CT and PET images may be gated against some physiological process such as breathing, or acquired dynamically to capture a biological process of the subject as a function of time. In other situations, multiple acquisitions may be made in the same sitting of different parts of the body.

It is typical to consider each such group of images as forming a single group or set, for storage, transmission, display and manipulation purposes.

The groups may be given different names, according to the context and type of acquisition. For example:
(i) Multiple MRI scans are referred to as 'multi-sequence' MR;
(ii) In CT, multiple static scans are referred to as 'multi-phase' CT. Multiple static scans may, for example, be taken in order to capture the progress of an injected contrast media through the organ. For cases where multiple CT scans have been acquired of different areas of the body in the same sitting, the set is called 'multi-series'.

In the remainder of this document, such datasets will be referred to, in the general case, as 'multi-volume datasets'.

Many known medical image workstations provide good tools to display and manipulate single 3D volumes. More challenging is the problem of display and manipulation of multiple 3D volumes. For example, the user may wish to load and visualise 3D scans acquired from different scanners, e.g. a CT and MRI scan of the same patient. Alternatively, the user may wish to compare the same type of scan taken at different points in time, for example to assess the change in disease over time, or to measure response to therapy. One or both scans may comprise multi-volume datasets.

Considering first datasets that are not multi-volume, on requirement is to align the images. These are pairs of images taken from two different datasets, for example an MRI scan and a CT scan of the same patient.

The process of aligning images is known as 'image registration'. Rigid, affine and deformable image registration methods shown in FIG. 1 can be used to correct for differences, to various extents. Use of these image registration techniques therefore makes the assessment of aligned images an easier process.

Known methods for aligning pairs of images are shown for example in references [1] and [2]. Commercial software is available to perform such alignment automatically. For example, Mirada XD3 available from Mirada Medical Ltd. is one such software application.

Another attribute of such software packages is the ability to create both 'fused' and 'side-by-side' displays of the aligned images. In the fused display, one image is shown in a view and another image shown as a semi-transparent overlay on the same view. In this case, in known systems, the overlay image is typically transformed and resampled according to the alignment calculated by the registration method. Side-by-side displays show the aligned datasets in non-fused views. However, they "bind" the scroll and zoom controls of the displays, such that they are always displayed in alignment. Some software tools also place a cursor or cross-hair on each display, and keep these in alignment as the user adjusts them.

Most modern workstations allow the user to configure the size and the position of the MPR views in a manner of their choosing. The MPR views may also be referred to as "hanging protocols" in the field of medical imaging.

When two or more datasets are loaded and are to be displayed simultaneously, it is useful to bind the display parameters such that they are correlated or synchronised. For example, when viewing multiple CTs taken over time, the two or more datasets each comprise a set of CT images taken at one sitting. It is useful to bind the zoom and pan settings of the views, such that the corresponding anatomical locations in the CTs can be visualised simultaneously. Display controls such as Window and Level, analogous to brightness and contrast controls, are also useful to bind under certain situations.

The challenges of display and manipulation of single and multiple 'multi-volume' datasets are greater still.

A typical example might be where one dataset is a multisequence MRI scan, consisting of images acquired in at least two different orientations. A second dataset to be displayed at the same time as the first might be a CT scan taken of the same subject. Such a multi-sequence MRI dataset may use different imaging parameters for the different sequences, or different MRI sequences within the dataset may typically relate to different parts of the body. Conventional approaches to display and manipulation of one view from the MRI scan and one form the CT scan will not work well.

In general, where at least one of the images in the view is from a multi-volume dataset, known approaches often result in sub-optimal views being displayed. This limits the information that may be derivable from the displayed images.

For example, consider the case where a multi-sequence MRI dataset is to be shown in a fused display with an overlay of a CT scan. Each image in the MRI set may consist of a different orientation. Displaying them only in a single pre-defined orientation will produce a poor quality display. Common MRI protocols used in diagnostic practice typically acquire a set of thickly sliced images. These images have a much greater spacing between images than the voxel size within each image slice. Such images would be best viewed in their original orientation. However, since each image may have a different orientation, the view on known displays cannot be configured to produce good quality displays.

The side-by-side views available in conventional software offer an alternative display of the datasets. However, once again, the user of known systems is required to pre-define or pre-set the orientation, before loading the data. As the user then selects different MRI sequences for display, the orientation of both the MRI display and that of the CT image will not be optimal, nor correspond.

The consequence of these shortcomings is that the user will spend a great deal of time adjusting the zoom, pan and orientation of the display in order to try to visualise their data properly.

REFERENCES

[1] 'CT-MRI image fusion for delineation of volumes in three-dimensional conformal radiation therapy in the treatment of localized prostate cancer'. G. L. Sannazzari, R. Ragona, M. G. Redda, F. R. Giglioli, G. Isolato and A. Guarneri. British Journal Of Radiology 2002; 75:603-607

[2] 'Medical image registration'. D Hill, P Batchelor, M Holden and D Hawkes. Phys Med Biol 2001; 46:R1-R45

BRIEF DESCRIPTION OF THE DRAWINGS

FIGS. 1-3 each show a prior art form of image registration.

FIG. 4 shows an illustration of images that may be displayed in sequence, with an embodiment of the present invention.

FIGS. 8 and 9 are tables, each showing details of three 3-D scans.

DETAILED DESCRIPTION

Figure 5:
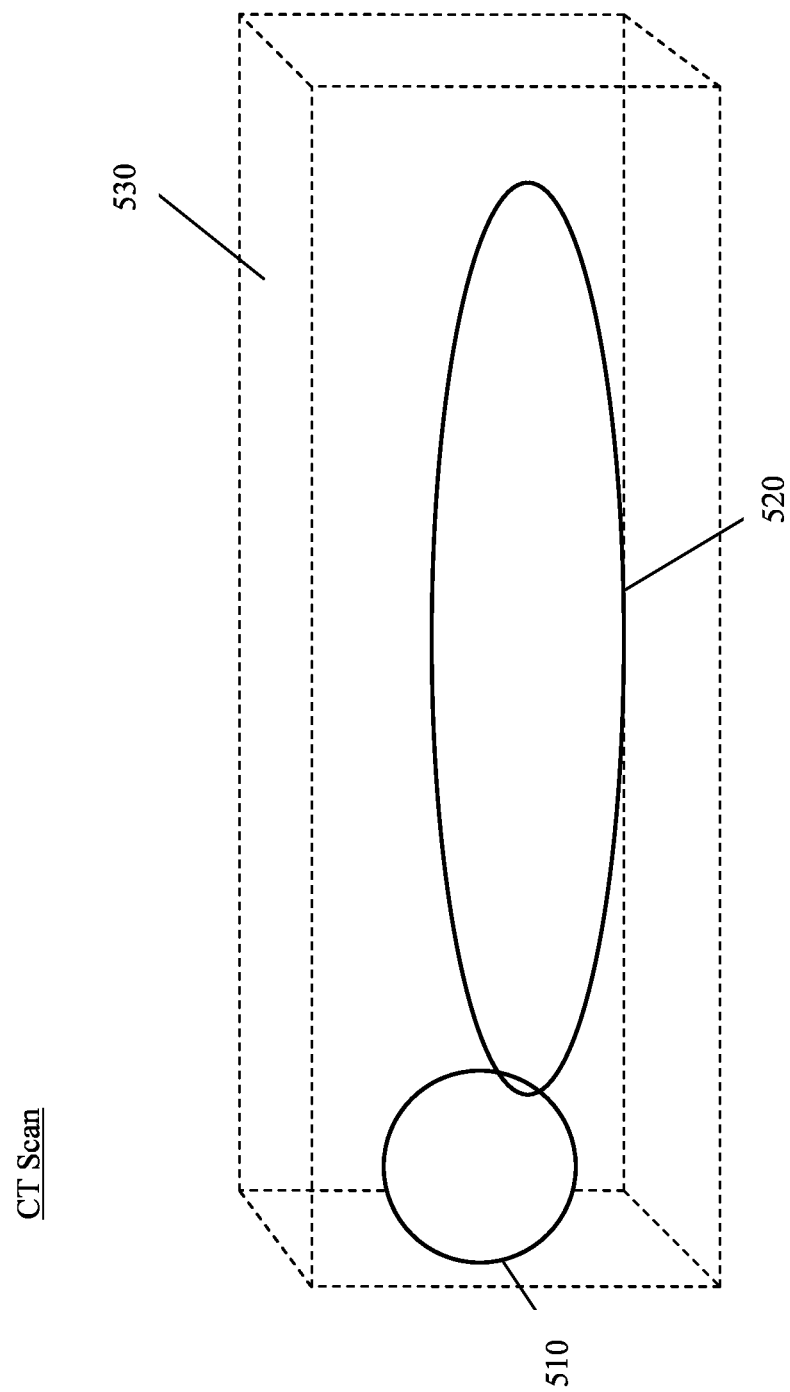
FIG. 5 shows an illustration of a CT scan volume.

The present invention provides control logic and a display that can dynamically adjust the viewing properties of displays of images derived from medical scan datasets. This may be achieved in a consistent manner.

The invention may provide more detailed views than prior art systems, when starting with the same medical scan datasets. The invention may automate some tasks, thereby speeding up the process of displaying high quality images of multiple datasets.

Firstly, the following example is used to illustrate the detailed explanation that follows the example. Consider the case where a user of a medical imaging workstation has loaded two datasets obtained from scans of the same 3D object. The scans were obtained using different modalities. These may be, in this example:

(i) A multi-sequence MR; and
(ii) a CT scan.

One or both datasets may be subjected to a full volume reconstruction.

In this situation, one image derived from the multi-sequence MR dataset will be displayed simultaneously with one image derived from the CT scan dataset. A transformation is used to map locations in each MR image with locations in the CT image that is displayed together with that MR image.

As discussed in the background section, such a transformation may be determined through the use of a registration algorithm. The transformation may be of the rigid, affine or deformable type, as shown in FIGS. 1-3. Typically, all of the MRI slices in the dataset are acquired in the same sitting, and therefore the mutual relationship between each of these is known.

With an embodiment of the invention, the user is presented with pairs of views in sequence. Each pair comprises an image from the MRI dataset, and an image from the CT dataset. In this example, the MRI dataset is a multi-sequence dataset, i.e. an example of a multi-volume dataset. So the MRI dataset itself includes:

(i) At least one series of 2D slices taken in a given direction, such as axially; and
(ii) At least one more series of 2D slices. The at least one more series of 2D slices includes slices that were taken in a different location of the scanned object, and/or in a different direction, such as coronally.

FIG. 4 shows examples of the pairs of images that are provided in this example. FIG. 4 shows a 'side-by-side' display, rather than a fused view with one image overlayed on the other. In FIG. 4, images 410, 430, 450 and 470 show consecutive images derived from the MRI dataset. Each image is one slice from the multi-sequence set. Images 420, 440, 460 and 480 each show an image of a slice of the CT dataset.

In this example, images 410 and 420 are displayed together, simultaneously. After images 410 and 420 have been displayed, images 430 and 440 may be displayed together. Then images 450 and 460 may be displayed together. Finally, images 470 and 480 may be displayed together.

Image 410 from the MRI set is displayed simultaneously with image 420 from the CT dataset. Object 415 in image 410 is a representation of a cross-section through a 3-D object, such as an organ in a patient. Object 425 in image 420 corresponds to object 415. Henceforth the term 'object' should be construed widely, and may typically mean a larger volume of tissue than just an organ, for example, the object may be a whole human subject.

Image 410 corresponds to one acquisition plane of a first volume of the MRI dataset. Given that there may be a significant separation between the slices that make up the MRI dataset, this is important. It means that object 415 will be shown with the highest resolution possible from the voxels of the original dataset that was acquired. Image 410 results from performing a full volume reconstruction for either the entire MRI dataset, or the first volume of the MRI dataset.

Once image 410 has been derived, it can be displayed. Image 420 derived from the CT dataset results from determining a surface through the CT volume that corresponds in some way to that of image 410 i.e. the acquisition orientation of the first MRI dataset. This may be achieved through the use of a transformation that maps datapoints in MRI volume to datapoint in the CT dataset. Such a transformation may be obtain through the use of a registration algorithm. Images 410 and 420 both lie in the same plane, which is the plane of acquisition of image 410. Clearly, if a deformable registration exists between the MRI and CT volumes, then the plane in the MRI would be planar, whereas it might map onto a curved surface in the CT. An alternative is to select the plane in the CT that corresponds to the plane with the same orientation as image 410, pivoted at a location found through the use of a deformable registration.

Images 410 and 420, and hence object representations 415 and 425, can then be displayed simultaneously.

Subsequently, image 430 from the MRI dataset and image 440 from the CT dataset may be derived, and displayed simultaneously. The object shown as 415 in image 410 is also visible on view 430, as object 435. However, the plane of view of image 430 is different from that of image 410. So the object 435 may, for example, be slightly smaller than object 415. This might occur if image 430 were in a plane parallel to the plane of image 410, but at a location further along the organ than the location in which images 410 and 420 were taken. If the organ were tapering, i.e. had a smaller cross-sectional area in the plane of the image 430, then it would appear smaller as object 435 in image 430. In this example, images 410 and 430 are successive, parallel images from the first volume of the multi-sequence MRI dataset.

Image 440 is derived from the CT dataset, and lies in the same plane as image 430. Object 445 would therefore also be slightly smaller than object 425, as shown.

If the plane of images 410 and 430 corresponds to the plane of acquisition of the CT dataset, then images 420 and 440 may need simply to be selected from the CT dataset. However, in general terms, images 420 and 440 will result from a re-slicing of the CT dataset, which can only be done once the acquisition planes of images 410 and 430 are known. If images 410 and 430 are from an MRI scan, and were acquired in planes specified by a user that did not correspond to axial, coronal or saggital, then the CT dataset will need to be re-sliced. After this re-slicing, images 420 and 440 will be in planes that correspond to the acquisition planes of images 410 and 430.

After display of image pair 430 and 440, the next pair of images displayed is 450 and 460. Image 450 from the MRI dataset shows object 455, which is slightly smaller than object 435. Image 450 may be in an acquisition plane parallel to images 410 and 430, and be further along a first volume of images than image 430. Image 460 is from the CT dataset, and is in a plane corresponding to the acquisition plane of image 450.

After display of images 450 and 460, images 470 and 480 are displayed. Image 470 is from a second image series of the MRI dataset. It may show a completely different object 475 than objects 415, 435 and 455. Object 475 may be either:
(i) From a completely different part of the body than objects 415, 435 and 455;
(ii) A view taken along a different axis than was used to take the 2D scans of the first series that showed objects 415, 435 and 455.

Image 470 may be selected by a user, who has seen enough of the first series of images once images 410, 430 and 450 have been displayed. However, image 470 may be displayed automatically, once the last of the images in the first series f the MR scan has been displayed.

In a real world example, objects 415, 435 and 455 may be three views of the liver of a patient. These may, for example, show tumours. Image 470 may be from a second series of the MRI scan, showing the head of the patient. The user may select image 470, in order to be able to check the head for 'secondary' tumours. As each of objects 415, 435, 455 and 475 is displayed, the simultaneous display of images 420, 440, 460 and 480 will enable the user to see the information derivable from the CT scan of the whole patient, in the same plane.

Acquisition View

The invention introduces a new type of view, which is termed the 'Acquisition view'. The Acquisition view synchronises the orientation of the view on the display to that of the orientation of the dataset being viewed. The orientation may simply correspond to one of the standard orientations 'axial', 'coronal' or 'saggital', or may be some other angle, a so-called 'off-axis' views.

As the user switches to a next image for display, whether that is from the same or a different volume of the dataset, the Acquisition view adjusts the view orientation to match the orientation of the dataset, such that the user is always viewing data in its acquired orientation. The benefits for users may be greatest when switching to display of the next volume of the multi-volume dataset. This next volume may be the next series of a multi-series MRI dataset, or may be the next phase of a multi-phase CT scan dataset.

In medical imaging, hybrid scanners can now provide a combined MRI and CT scan of a patient, at one sitting. Alternatively, they may provide a combined MRI scan and a PET scan. Some scanners may provide each of an MRI, CT and PET scan dataset, and one or more of these may be a multi-volume dataset. The present invention may help with the manipulation and detail of view available from these datasets.

The invention may provide advantages for MRI where the in-plane resolution, that is the resolution within each acquired slice, is typically much higher than between slices. For example, each voxel of an MRI slice may be 0.5 mm or less within the slice. However, it may be 5 mm or 8 mm between slices. Therefore, for optimal display MRI datasets are best viewed in their acquisition orientation. Such coarse 2D slices may be treated in conventional scanners and medical imaging workstations in the same way as other scans, such as CT, which have fine resolution both in the plane of acquisition and with finely spaced planes of acquisition.

Note that many conventional workstations do allow the visualisation of 2D MRI slices. However, these treat the MRI dataset as 2D images, and do not perform any volume reconstruction. For registration with other 3D datasets, the present invention can perform full volume reconstruction, and be able to display MRI in their original orientation.

The invention may provide the Acquisition as a new type of view, available for user selection. Thus the Acquisition view may be one of a set of views offered to a user, for selection. That set may, for example, the options of: 'Acquisition view'; 'axial'; 'coronal'; 'sagittal'; and 'user-defined'.

However, the 'Acquisition view' may be offered to a user, e.g. as a menu option on an interactive display screen, in place of one of the conventional MPR orientations typical in conventional workstations.

The Acquisition view may optionally automatically adjust its field of view, to ensure that the image is always in view in each image, as the user switches between the datasets.

The Acquisition view may also be used in fused views. Unlike conventional fused views where the orientation of the views for all layers in the view are pre-defined or are controlled manually by the user, the Acquisition fused view always displays both layers in the same orientation as the orientation of one of the images in view. In an implementation of the Acquisition view, the image in the base layer defines the orientation of the fused view.

FIG. 5 illustrates a CT scan. The object to be scanned is made up of torso 520 and head 510. The object may instead be a whole body, or a smaller region of a body.

The large cuboid 530 illustrates the volume for which scan information is obtained by the CT scanner. The 'dataset' 530 is a series of datapoints, located in 3-Dimensions.

FIG. 5 shows a single dataset 530. However, a marker substance may be injected into a patient 520/510. In this case, one CT 'phase' may be taken prior to the injection, a second 'phase' may be taken just as the injection is carried out, and a third CT 'phase' may be taken 5 seconds or so after the second phase. Thus the resulting CT dataset is a multiphase dataset, with three phases each covering the same spatial extent and taken in the same direction. Typically, a CT scanner will take axial slices.

Figure 6:
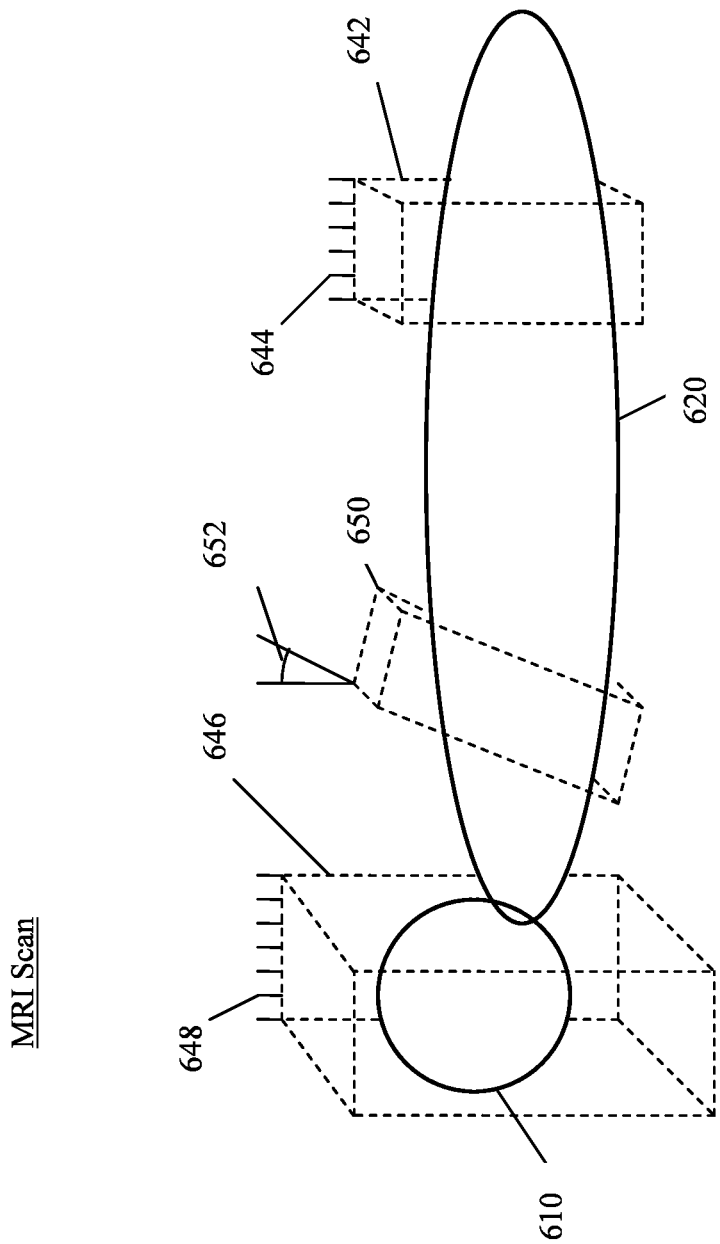
FIG. 6 shows an illustration of a multi-volume MRI scan.
Figure 7:
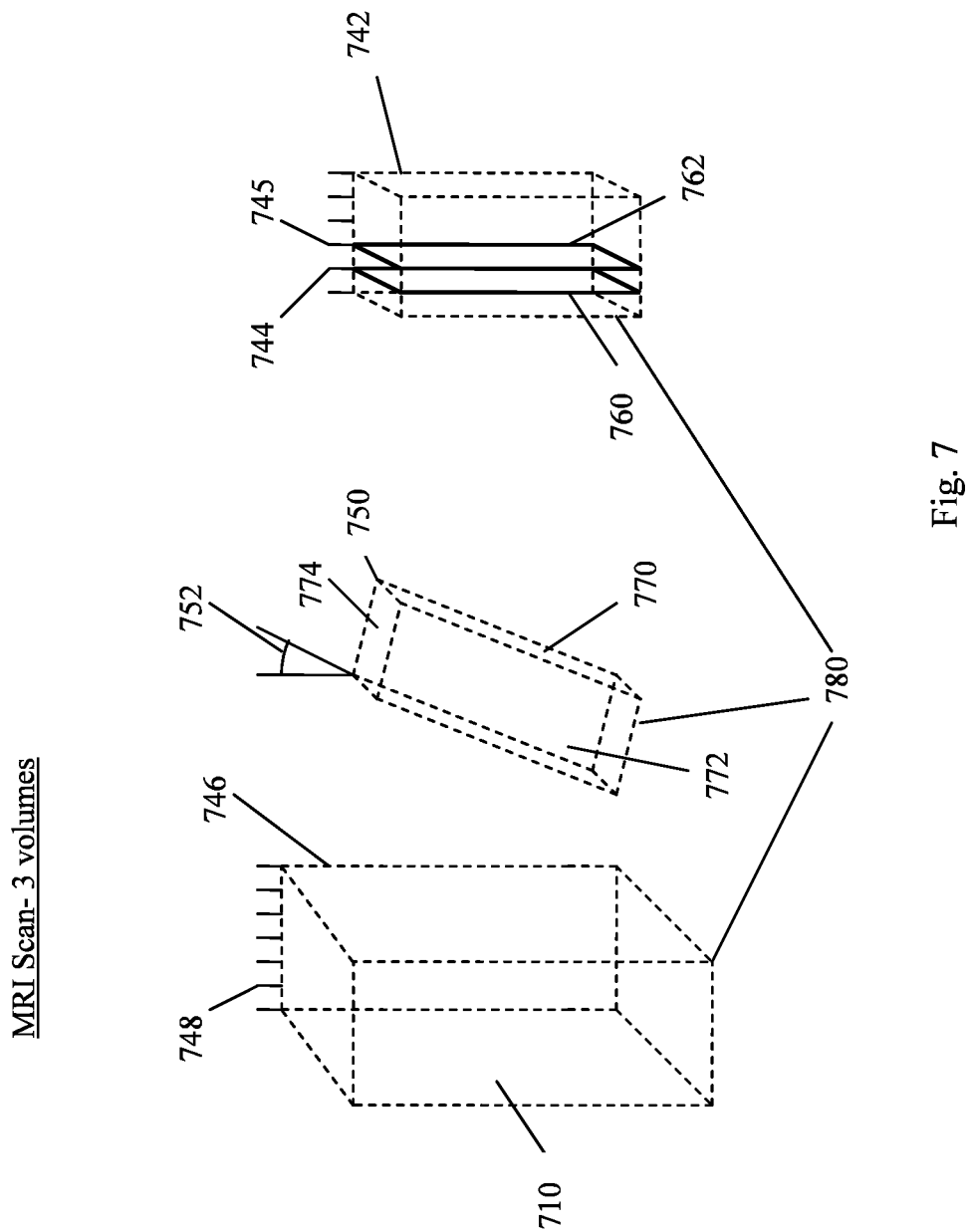
FIG. 7 shows further detail of the scans of FIG. 6.

FIGS. 6 and 7 illustrate a multi-series MRI scan. Object 610/620 corresponds to that in FIG. 5.

The MRI scan comprises:
(i) A first series of 2D slices making up a first volume, which is shown as cuboid 642. This series may show the abdomen.
(ii) A second series of 2D slices making up a second volume, which is shown as cuboid 646. This series may show the head 610.
(iii) A third series of 2D slices making up a third volume, which is shown as cuboid 650. This series may show the upper chest.

First series 642 may comprise a series of axial 2D slices, whose locations are shown by the short lines 644 along the top of the cuboid 642. Similarly, second series 646 may comprise a series of axial 2D slices, whose locations are shown by the short lines 648 along the top of the cuboid 646.

The third series 650 may be made up, for example, of 2D slices that are in panes parallel to any of the faces of cuboid 650. Clearly, these will not be axial slices. Angle 652 shows that cuboid 650 is tilted, and none of the faces of cuboid 650 has a normal that lies in the axial direction of object 610/620.

FIG. 7 corresponds to FIG. 6. However, FIG. 7 shows just the three volumes, with references 742, 746 and 750, as they may be provided as an input to the method and system of the present invention. Label 780 shows the three components, i.e. the three volumes, of the multi-series dataset that results from the MRI scan in FIG. 6.

Within first volume 742, two 2D slices have been shown. These are 2D slices 760 and 762. These 2D slices are axial slices, which located at points 744 and 745, indicating parallel planes. Similar axial slices may make up second volume 746, and be located at points 748.

The 2D slices in third series 750 may lie in planes parallel to the nearest face 772. However, the slices may lie in planes parallel to the face 770, shown to the right of volume 750. Alternatively, the 2D slices may lie in planes parallel to top face 774 of volume 750. In each of these cases, the 2D slices will not be axial.

FIGS. 8 and 9 show tables, each illustrating examples of three 3-D scans.

In FIG. 8, scan 1 is a multi-series MRI scan. The three volumes of scan 1 are all of the head, but are taken in three orthogonal directions.

Scan 2 is a CT scan comprising two phases, both also of the head. Both phases are taken axially, as were the 2d slices that make up the first volume of the $1^{st}$ scan.

Scan 3 is not a multi-volume scan. It is also of the head, but is an axial PET scan.

With conventional hybrid scanners and medical imaging workstations, the user is left to try and derive useable data from scans such as those in the table of FIG. 8. With the invention, the plane of acquisition of, for example, any image derived from one of the MRI series can:
(i) be displayed in its original acquisition orientation; and
(ii) be displayed together with images from the $2^{nd}$ and $3^{rd}$ scans that have been selected or automatically re-sliced, so that they are in the same plane as the image from the MRI series.

Conditions (i) and (ii) will apply not only to images from one of the MRI series, but can also apply when a user selects an image from a different one of the three MRI series. If the user chooses, the images from the first and third scans can, for example, be from the same plane as the plane of acquisition of an image from one of the phases of the CT scan. So the user can select which scan will be used as a basis for selecting/re-slicing images from the other two datasets.

The table of FIG. 9 shows a more unusual set of scans than in table 8. Here the $1^{st}$ scan is a multi-series MRI dataset. However, each series is for a different part of the object. The different parts are three organs/regions: head; heart and pancreas. This contrasts with the table of FIG. 8, where each series in the MRI dataset was for the same part of the object, but taken in an orthogonal plane to the other two series.

In FIG. 9, the two CT phases provide 2D slices of the whole object, i.e. the whole body. So, whatever image is selected from any of the three series of the MRI multi-series, an image can be selected or re-sliced from one of the CT phases and will be in the same plane as the image from the MRI series. This is important, since the second series of the MRI multi-series dataset is taken at an angle that does not correspond to axial, coronal or saggital.

The coverage of the $3^{rd}$ scan, the PET scan, is limited to the head. So the invention may only display three images, simultaneously, when the first series of the MRI dataset is being displayed, i.e. when the user is examining images of the head. When an image from the second or third series of the $1^{st}$ scan is being displayed, there is no image that can be generated of the same part of the object, from the $3^{rd}$ scan. This is because the third scan did not encompass the heart and pancreas.

New Binding Types

In addition to the conventional view bindings available in convention medical image workstations, the invention introduces three new display binding types: field of view binding, orientation binding and dataset binding. Each of these is discussed below:

Field of View Binding

The field of view determines the extent of the 3D scan, and ultimately the extent of the anatomy being viewed. In conventional workstations, the field of view can be manually adjusted through the zoom and pan controls. In this invention, the field of view is directly bound to that of other views.

In the context of the CT-MR example above in FIG. 5-7, as the user switches between each of the images in the MRI dataset 780, the field of view for the view displaying an image from the CT dataset 530 is adjusted automatically, such that it correlates with that of the MRI image being displayed. In this manner, whatever the field of view of the particular MRI image currently being displayed in the view, the CT always stays correlated. Thus the user can easily compare the image of the CT with that of the MRI, without needing to perform manual adjustments.

As a more concrete example, suppose that the MRI set comprises a first series covering the lung, and another set of slices of the pelvic area. Using a conventional workstation, the user would be required to re-adjust the zoom and pan of the CT view when switching between the lung and pelvic MRI series, i.e. deciding to select an image from the other series. This is time consuming. Using the invention, this is automatically adjusted, saving a great deal of time.

Conventional systems do have zoom and pan bindings. However, with the invention, the field of view is automatically synchronised on bound views, when the user changes the image being viewed in a multi-volume set.

Orientation Binding

The orientation of the view of the image determines the orientation of the slice through the 3D volume. When viewing images from multi-volume scans at the same time as images from other types of scan, it is important that the view orientation is synchronised such that the user can be sure that they are examining images from the same anatomical section in all scans. This is referred to as 'Dataset Driven Orientation Binding'.

In the context of the CT-MR example of FIG. 5-7, as the user switches between each of the images derived from the MRI set, the orientation for the view displaying the CT is adjusted automatically, such that it correlates with that of the MRI image being displayed. It is typical that different MRI image series from a multi-series MRI dataset will comprise images with different orientations. This capability is particularly advantageous for such multi-series MRI datasets, as it ensures that the CT is always displayed in the same orientation as the MRI.

Another type of Orientation binding can be performed, where the user is performing a manual adjustment of the view orientation. For example, if the user has loaded several CTs taken over time to determine the change in disease as a response to treatment, the invention can keep the view consistent. Using a conventional workstation, any adjustment to the view orientation will not be synchronised, and the user must make appropriate changes manually. This may be error-prone, and time consuming.

Dataset Binding

In cases where several multi-volume datasets have been loaded, for example two or more multi-sequence MRI scans, the invention allows the user to make comparisons easily. The invention provides the capability of 'binding' the dataset being examined. As a consequence, as the user switches the view between the various datasets of the first multi-volume dataset, the corresponding dataset from the second multi-volume acquisition is shown.

In some cases, where different sequence sets have been acquired such that there are some images in the first set that do not correspond to the second set, the invention does not provide a binding.

Options

The invention may also bind curved MPR views. To do this, a deformable registration is used.

Combination of Options Available with the Invention

The various enhancements that may be provided by the invention, as described above, may be combined. This may provide a particularly practical and powerful solution.

Consider the case where the user has loaded a multi-sequence MR, and a CT scan. The example also works for the case where the user has loaded a multi-sequence MR dataset and a PET/CT dataset, where the PET and CT have been acquired by a hybrid scanner and hence are in alignment (assuming that the patient has not moved between the sequential scans).

A transformation is required that maps locations in each MR image in the set with locations in the CT. As discussed above, such a transformation may be determined through the use of a registration algorithm and may be of the rigid, affine or deformable type. Typically, all of the MRI images in the set are acquired in the same sitting, and therefore the relationship between each of these is known.

The user is presented with views of images from the MRI images and the CT on the display. Most modern workstations allow the user to configure the size and the position of the MPR views, or "hanging protocols" as they are termed in the field of medical imaging, in a manner of their choosing. For this example, consider a simple display shown in FIG. 4, where the view 410 on the left shows a slice of one of the MRI images in the multi-sequence set, and the image on the right shows a slice of the CT 3D scan.

The invention applies control logic to the views of the data, such that the user is always shown an image from the different modalities that correspond to the same anatomical section. The invention may achieve this behaviour by synchronising a number of properties of the display and performs the following steps.

Step 1) The invention allows the user to load all the data selected by the user. In the example above, this includes the CT (or PET/CT) and all of the sequences of the MRI dataset (which can be one or more).

Step 2) The invention allows the user to define layouts in their preferred arrangement. The user can pre-define the orientation of the MPR slice views, as with conventional workstations. However, the user can also define a new view type, the Acquisition View, which automatically sets the view orientation to that of the acquisition orientation of the MPR dataset being viewed. As the user selects the different images within the MRI multi-sequence set, the orientation is automatically adjusted.

In this manner this new view type allows the user to navigate the 3D volume while always viewing the MRI image in its optimal manner.

Note that, it is possible to acquire an MRI series in a manner that the view orientation changes across the acquisition. Hence the slices within the volume have different orientations. The invention can account for this, and adjust the view orientation as the user navigates through the slices.

Step 3) The invention can, at the user's preference, automatically adjust the view orientation of the CT (or PET and CT) such that they are always in the same orientation as the particular MRI image viewed in the MRI Acquisition view. As the user selects the different images within the MRI multi-sequence series, the orientation of the CT (or PET and CT) are automatically adjusted such that they are always in the same orientation.

The invention may optimally also operate to keep the orientation of the MRI synchronised with that of the CT (or PET and CT). That is, all the bindings may be configured to operate symmetrically.

Step 4) Optionally, the invention may also adjust the field of view of the CT (or PET and CT) to match that of the particular MRI image selected for viewing by the user. As the user selects the different images from the MRI multi-sequence set, the field of view of the CT (or PET and CT) are automatically adjusted to match that of the MRI. The field of view is defined by the pan and the extent of the display.

For example, if two MRI image series comprise a thoracic scan and pelvic scan, then, as the user switches from one to the other, the CT panning, zoom and extent of the display are adjusted to show the same part of the anatomy as that shown in the MRI image selected by the user. Alternatively, any other parameters required to define the field of view of the display in a particular implementation may be adjusted.

Curved MPR Orientation Binding Option

A curved MPR is an MPR slice whose normal vector follows a curve, instead of a line, through the 3D volume. In essence it is a view that adjusts the view orientation for each slice according to a pre-defined curve. This type of view may be advantageous where the clinician needs to visualise a structure that curves through the body, such as a vessel or vertebral structure, because the view orientation is always kept normal to the orientation of the structure.

The curve is usually defined by the user or found through the application of a specific algorithm. The invention may be extended to bind the orientation of curved MPRs across multiple datasets. This is achieved by mapping the curve to the other datasets to be viewed using a registration—a transformation which maps locations in one dataset to locations in another. For example, a deformable registration mapping the datasets could be used for this. Given the mapped curved, each view can look-up the appropriate orientation, by calculating the normal to the curve defined on its corresponding dataset.

The registration between the datasets may be rigid, affine or another parametric transformation, or deformable. It may be calculated by using a conventional registration algorithm, using just the images. Alternatively, an attempt can be made to map MPR curves, defined on each or some of the datasets whose views are to be bound. For example, an MPR curve can be defined by the user on each of the datasets. This may be used in full or in part to define or estimate a deformable registration between the datasets.

Figure 10:
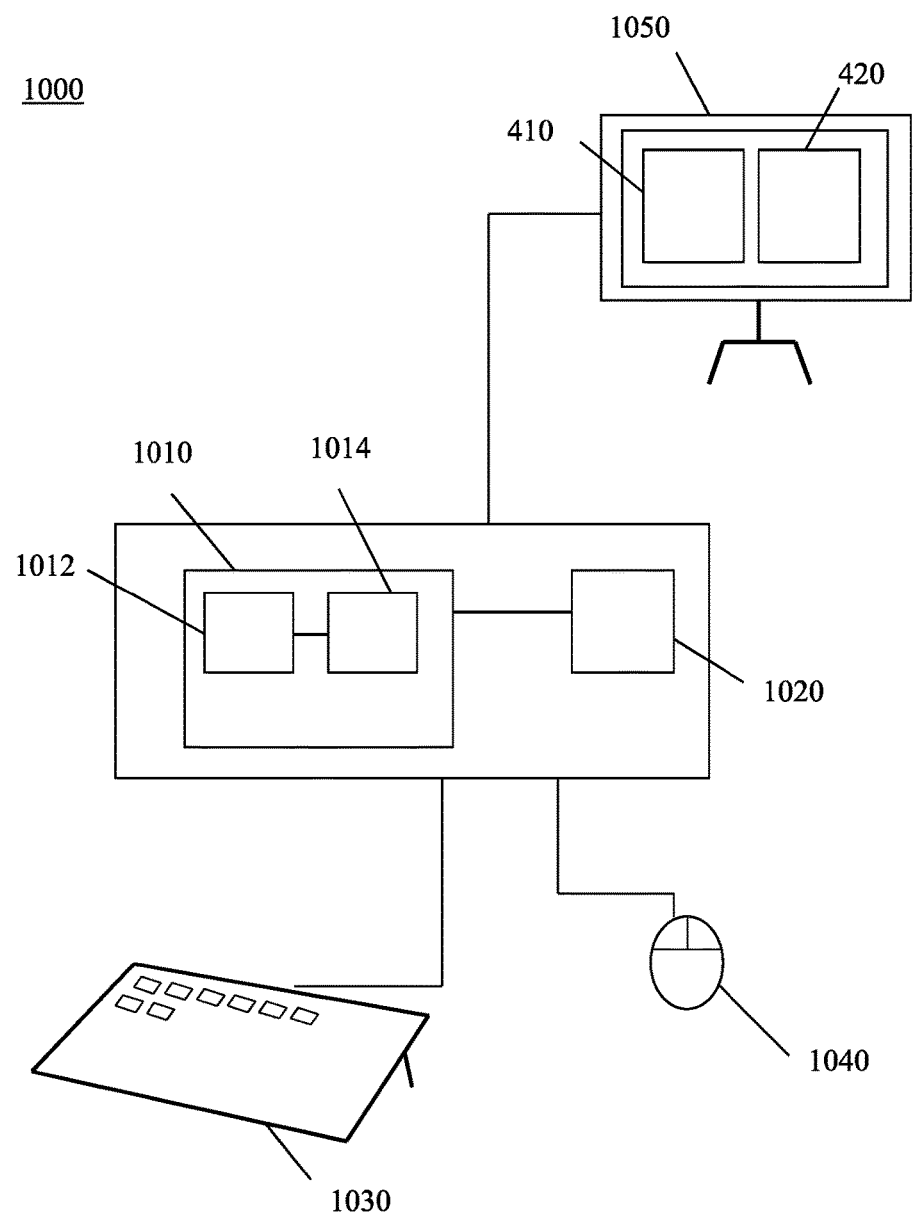
FIG. 10 shows an embodiment of a medical imaging workstation in accordance with the invention.

FIG. 10 shows a workstation 1000 for implementing a method of displaying medical images in accordance with the invention.

Keyboard 1030, mouse 1040 and display screen 1050 facilitate communication with a user of the medical imaging workstation. An interactive touchscreen may be included.

First subsystem 1010 of workstation 1000 may be implemented for example as signal processing logic 1012 and memory 1014. First subsystem 1010 allows a user to load and store:(i) A first (780) medical scan dataset obtained by scanning a 3-dimensional (3-D) object with a first scanning modality; and (ii) a second (530) medical scan dataset obtained by scanning the 3-dimensional (3-D) object with a second scanning modality.

Analysis module 1020 allows the creation and simultaneously displaying of medical scan images. Analysis module may:
(i) derive a first image (410) from the first (780) medical scan dataset, the first image lying in a first plane, the first plane corresponding to an acquisition plane of the first (780) medical scan dataset;
(ii) obtain a second image (420) from the second medical scan dataset (530), the second image lying in the first plane.

The first image (410) and the second image (420) may be displayed simultaneously. The user input means 1030, 1040 allow the selection of medical scan images for display, and allow the user to decide which medical scan image(s) to display at a given time.

Figure 11:
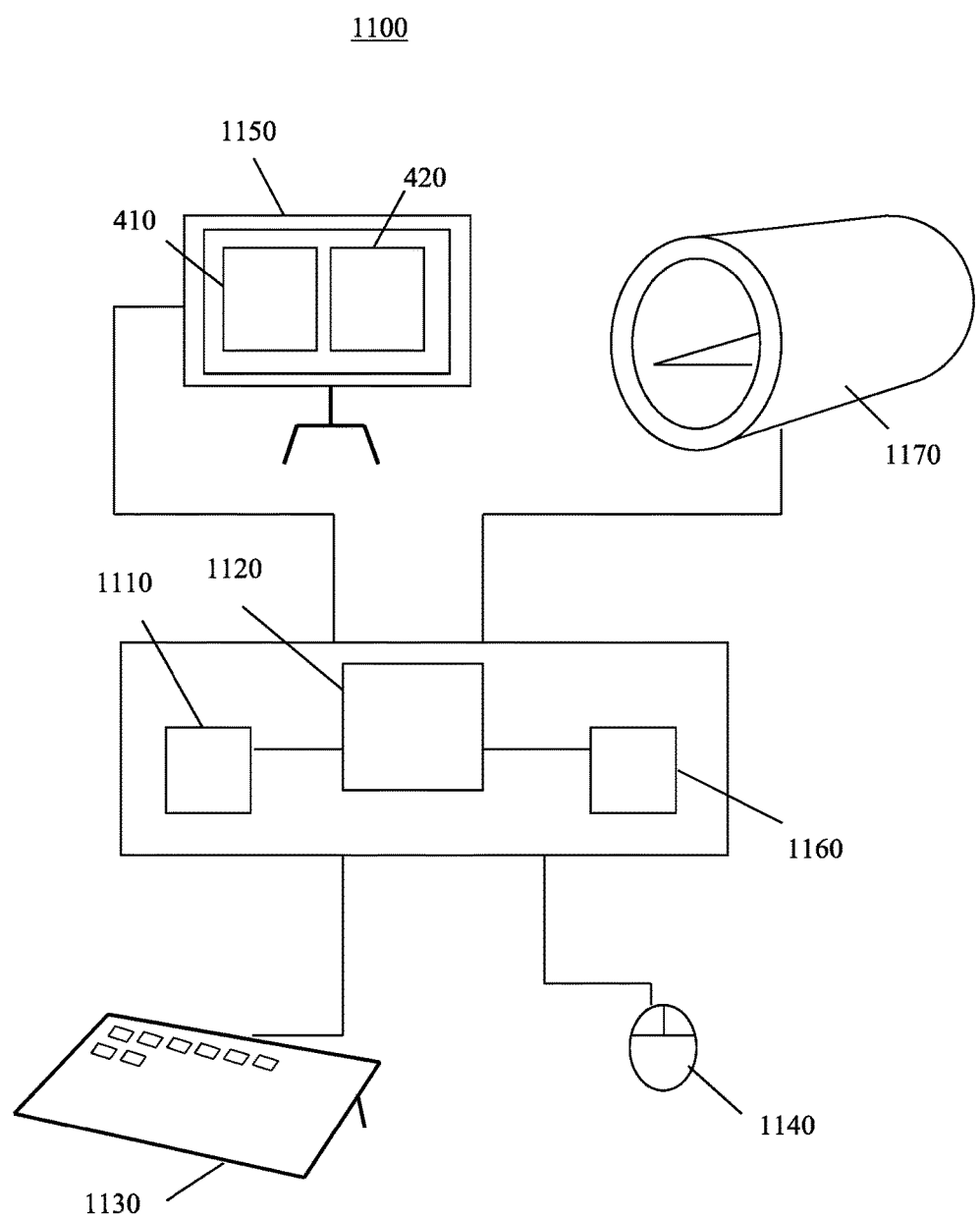
FIG. 11 shows an embodiment of a hybrid medical imaging scanner in accordance with the invention.

FIG. 11 shows a hybrid scanner 1100 in accordance with the invention. Hybrid scanner 1100 has some analogous components to those described in FIG. 10 for a medical imaging workstation 1000. Keyboard 1130, mouse 1140 and screen 1150 facilitate communication with a user of the hybrid scanner 1100.

Hybrid scanner 1100 comprises:
a) A control module 1160 that controls a scanning unit 1170, to provide a first scan dataset and a second scan dataset. These may be images of tissue, of a subject inside scanning unit 1170. The first and second scan datasets are produced using different scanning modes. Multi-volume datasets using the same scanning mode can also be provided.
b) A first subsystem 1110, which allows a user to capture and store:
(i) a first (780) medical scan dataset obtained by scanning a 3-dimensional (3-D) object with a first scanning modality; and
(ii) a second (530) medical scan dataset obtained by scanning the 3-dimensional (3-D) object with a second scanning modality.
c) Analysis module 1120, which allows the creation and simultaneously displaying on display 1150 of medical scan images. Analysis module 1120 may:
(i) derive a first image (410) from the first (780) medical scan dataset, the first image lying in a first plane, the first plane corresponding to an acquisition plane of the first (780) medical scan dataset;
(ii) obtain a second image (420) from the second medical scan dataset (530), the second image lying in the first plane.

A computer program product in accordance with the invention has executable code for a method in accordance with the invention. The method may create and simultaneously display medical scan images, from each of:
(i) a first (780) medical scan dataset obtained by scanning a 3-dimensional (3-D) object with a first scanning modality; and
(ii) a second (530) medical scan dataset obtained by scanning the 3-dimensional (3-D) object with a second scanning modality; the method comprising:
deriving a first image (410) from the first (780) medical scan dataset, the first image lying in a first plane, the first plane corresponding to an acquisition plane of the first (780) medical scan dataset;
obtaining a second image (420) from the second medical scan dataset (530), the second image lying in the first plane; displaying the first image (410) and the second image (420) simultaneously.

Figure 12:
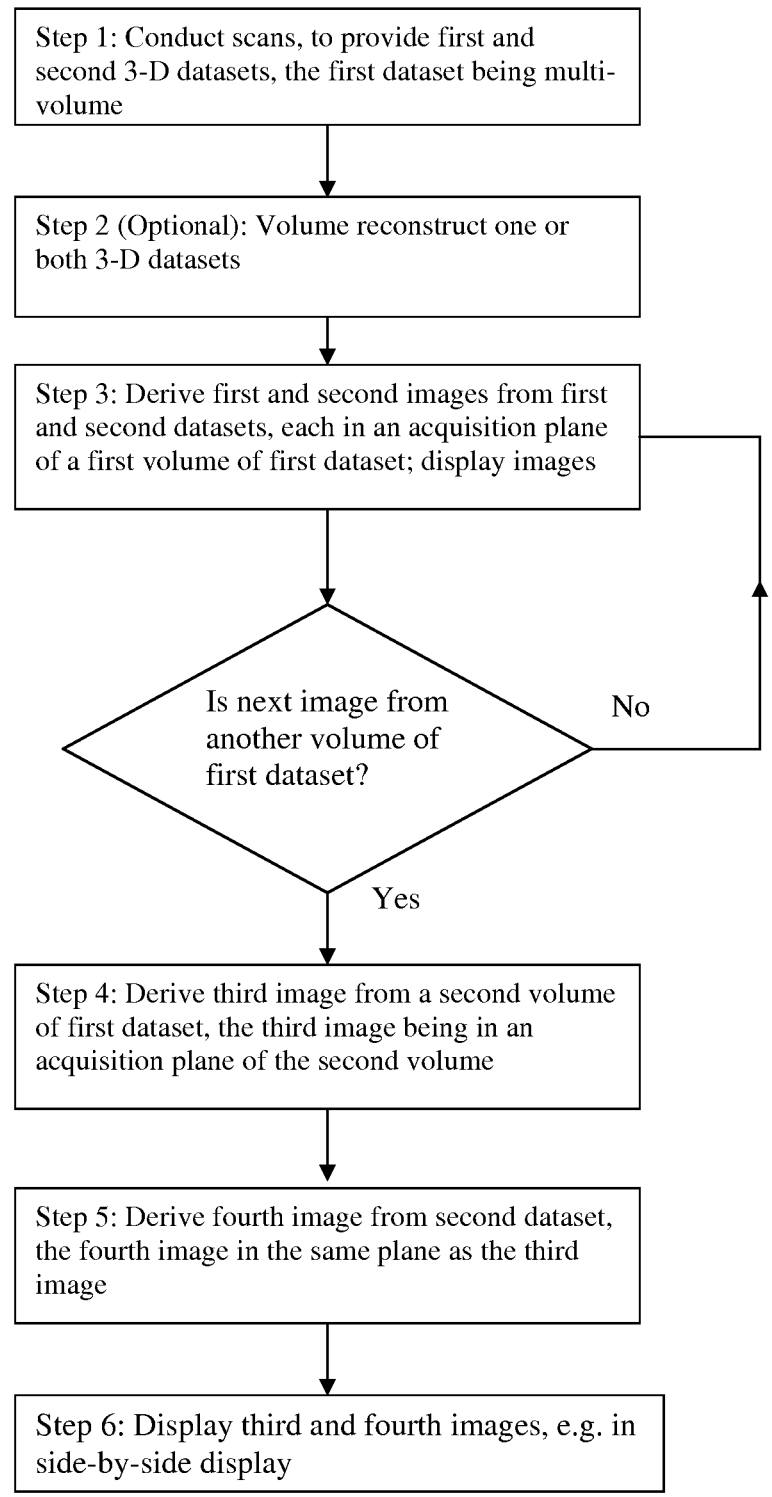
FIG. 12 is a flowchart of an embodiment of the invention.

FIG. 12 illustrates an embodiment of a method in accordance with the invention. In general, the method of the invention allows the creation and simultaneously display of medical scan images, from each of:
(i) a first (780) medical scan dataset, obtained by scanning a 3-dimensional (3-D) object with a first scanning modality; and
(ii) a second (530) medical scan dataset, obtained by scanning the 3-dimensional (3-D) object with a second scanning modality;

In accordance with the method, a first image (410) is derived from the first (780) medical scan dataset, the first image lying in a first plane. The first plane corresponds to an acquisition plane of the first (780) medical scan dataset.

A second image (420) is obtained from the second medical scan dataset (530), the second image lying in the first plane. The first image (410) and the second image (420) are displayed simultaneously.

The illustrative steps in FIG. 12 show:
(i) Step 1: Conducting the two or more scans. One or both scans may provide a multi-volume dataset.
(ii) Step 2: One or both scans may be volume re-constructed, prior to registration.
(iii) Step 3: The first (410) and second (420) images are derived, each in the acquisition plane of one of the images, in this case this is the plane of the first image (410). The images are then displayed.
(iv) A decision is then reached about whether to display a further image from a different volume than the volume that has so far been displayed. If not, then the method returns to step 3. If a new volume is to be used, then the method advances to step 4.
(v) Step 4: A third image (770) is then derived from the next volume of the first dataset.
(vi) Step 5: A fourth image (780) is then obtained from the second dataset, the fourth image being in the same plane as the third image.
(vii) Step 6: The third and fourth images are then displayed, in 'side-by-side' display mode.

After step 6, further images from the second volume of the first dataset may be displayed, with corresponding images from the second dataset. Alternatively, the user may choose another volume of the first dataset, including re-selecting the first volume, and select images from there.

There are various possibilities, regarding the timing of when the second and fourth images are obtained from the second dataset (530). The second image may be obtained, for example by re-slicing, once the user has chosen the first image for display from the first dataset. This may involve a delay, for re-slicing the second dataset. However, the invention may comprise a step of ascertaining which acquisition views are included in the first dataset, i.e. the planes in which each slice of the first dataset lie. This step may comprise ascertaining which acquisition views/planes are included in just one volume, or in more than one volume, where the first datset is a multi-volume dataset. For each acquisition plane of the first dataset, a corresponding image in the same plane can be derived in advance, and stored. Thus when a user selects any of images 410, 430, 450 or 470, the corresponding image 420, 440, 460, 480 may then already be immediately available for display, without any delay.

The pre-calculation of images may be particularly useful when there are two other datasets for display. A multiseries MRI dataset, for example, may comprise ten or more different series, each having tens or hundreds of 2d slices. The advanced computation in such cases may be time consuming, but still practicable.

Volume reconstruction may provide particular advantages, when an MRI dataset is to be displayed. An MRI datset, or any other datset for display, may be 'volume reconstructed' to create a 3D volume, from the 2D slices in the original scan. In a first step, a 3D volume is created. Then 2D slices from the scan are populated into the 3D volume. The size of voxels in the volume will correspond to the spatial extent covered by each datapoint of each 2D slice. The slice thickness in the 3D volume corresponds to the slice thickness of the 2D scan slices that were acquired in the scan. Volume reconstruction of the dataset may speed the re-slicing and other manipulation of the original scan datapoints, for display.

In addition to the method shown in the flowchart of FIG. 12, the invention may also provide methods of:
a) constraining a field of view;
b) binding the selection of the volume; or
c) binding the orientation of images.
These are summarised under subheadings a)-c) below.
a) Method of Constraining a Field of View
The method may allow the creation and simultaneous displaying of medical scan images, from each of:
(i) a first (780) multi-volume medical scan dataset, obtained by scanning a 3-dimensional (3-D) structure with a first scanning modality, the first multi-volume medical scan dataset comprising at least a first volume (710) and a second volume (750); and
(ii) a second (530) medical scan dataset, obtained by scanning the 3-dimensional (3-D) structure with a second scanning modality. The method further comprises:
displaying a first image (410) derived from the first volume (710) of the first dataset (780), the extent of the first image comprising a field of view derived from the first volume; and
displaying a second image (420), obtained from the second dataset (530), together with the first image, an extent of the second image being locked to the field of view.
The field of view may be the full field of view of the first volume.

In a further preferred embodiment, the method may comprise: displaying a third image (770) derived from the second volume (750) of the first dataset (780), an extent of the third image comprising a second field of view derived from the second volume; and
displaying a fourth image (780), obtained from the second dataset (530), together with the third image (770), an extent of the fourth image (780) being locked to the second field of view.
The second field of view may be the full field of view of the second volume.
b) Method of Binding the Selection of the Volume.
The method may allow creating and simultaneously displaying medical scan images, from each of:
(i) a first (780) multi-volume medical scan dataset, obtained by scanning a 3-dimensional (3-D) structure with a first scanning modality; and
(ii) a second (530) multi-volume medical scan dataset, obtained by scanning the 3-dimensional (3-D) structure with a second scanning modality;
The method further comprises choosing a volume of the first dataset (780), and binding the selection of the volume of the second dataset (530) to the chosen volume of the first dataset, whereby, when displaying a first image (410) from a first volume (710) of the first multi-volume medical scan dataset, an image will be displayed from a volume of the second dataset that corresponds to the first volume (710).
c) A method of Binding the Orientation of Images
The method may allow creating and simultaneously displaying medical scan images, from each of:
(i) a first (780) multi-volume medical scan dataset, obtained by scanning a 3-dimensional (3-D) structure with a first scanning modality, and
(ii) a second (530) multi-volume medical scan dataset, obtained by scanning the 3-dimensional (3-D) structure with a second scanning modality, the second medical scan dataset (530) comprising at least a first volume and a second volume.
The method may further comprise binding the orientation of at least a first image (410) derived from the first (780) multi-volume medical scan dataset and a second image (420) obtained from the second (530) multi-volume medical scan dataset, the first and second images being displayed together, whereby:
as a user switches between successive displayed images (410, 430) from the first dataset (780), the orientation of a displayed image (420, 440) from the second dataset (530) is adjusted automatically, such that the orientation for the displayed image (420, 440) from the second dataset (530) corresponds to the orientation of a currently displayed image (410, 430) from the first dataset (780).
The present invention may be used in, for example:
(i) Picture archiving and communication systems (PACS).
(ii) Radiological information systems (RIS)
(iii) Hospital information systems (HIS)
(iv) Advanced visualisation workstations.
(v) Imaging Acquisition Workstations.
(vi) Web based or cloud based medical information and image systems.

The invention claimed is:

1. A method of creating and simultaneously displaying medical scan images, from each of:
a first medical scan dataset, obtained by scanning a 3-dimensional (3-D) object with a first scanning modality, the first scanning modality being one of, or a combination of: Magnetic Resonance Imaging (MRI);

Computed Tomography (CT); Positron Emission Tomography (PET); X-Ray; Ultrasound (US); and Single Photon Emission Tomography (SPECT); and a second medical scan dataset, obtained by scanning the 3-dimensional (3-D) object with a second scanning modality, the second scanning modality being one of, or a combination of: MRI; CT; PET; X-Ray; US; and SPECT;

wherein the first and second medical scan datasets are 3-dimensional (3-D) datasets; and wherein at least the first medical scan dataset is a multi-volume dataset, comprising at least a first volume and a second volume of the 3-D object obtained by scanning the 3-D object in a single sitting of the first scanning modality; and the method comprising:

deriving a first image from the first volume of the first medical scan dataset, the first image lying in a first plane, the first plane corresponding to an acquisition plane of the first volume of the first medical scan dataset, the acquisition plane being an imaging plane used at the time of acquisition of the first volume of the first medical scan dataset;

obtaining a second image from the second medical scan dataset, the second image lying in the first plane; and displaying the first image and the second image simultaneously, wherein the method further comprising, upon a user selecting to switch to a view of an image from the second volume of the first medical scan dataset:

deriving a third image from the second volume of the first medical scan dataset, the third image lying in a second plane, the second plane corresponding to an acquisition plane of the second volume of the first medical scan dataset;

obtaining a fourth image from the second medical scan dataset, the fourth image lying in the second plane; and displaying the third image and the fourth image simultaneously.

2. The method of claim 1, further comprising:
obtaining the second image by re-slicing the second medical scan dataset, to derive an image comprising datapoints from the second medical scan dataset that lie in the first plane.

3. The method of claim 1, further comprising:
obtaining the fourth image by re-slicing the second medical scan dataset, to derive an image comprising datapoints from the second medical scan dataset that lie in the second plane.

4. A method in accordance with claim 1, further comprising:
performing a volume reconstruction of each of the first and second datasets; and
obtaining a transformation that maps datapoints of the first medical scan dataset into registration with datapoints of the second medical scan dataset.

5. A method in accordance with claim 1, further comprising:
performing a volume reconstruction of all datapoints of the second dataset;
at a time point prior to deriving the first image, performing a volume reconstruction of datapoints of the first volume of the first dataset, and obtaining a transformation that maps datapoints of the first volume of the first dataset into registration with the datapoints of the second dataset; and at a time point prior to deriving the third image, performing a volume reconstruction of datapoints of the second volume of the first dataset, and obtaining a transformation that maps datapoints of the second volume of the first dataset into registration with the datapoints of the second dataset.

6. A method in accordance with claim 1, further comprising:
displaying the first and second images in side-by-side view.

7. A method in accordance with claim 1, further comprising:
obtaining a fifth image and a sixth image from a third 3-D medical scan dataset, the fifth image being in the first plane and the sixth image being in the second plane; and
displaying the fifth image simultaneously with the first and second images; and
displaying the sixth image simultaneously with the third and fourth images.

8. A method in accordance with claim 1, wherein:
the first dataset comprises a set of 2-D slices, the acquisition plane of each slice being spaced from neighboring acquisition planes by a distance at least twice as great as the distance between datapoints within the slices.

9. A method in accordance with claim 1, wherein:
the first dataset is a multi-sequence MRI dataset;
the second dataset is a CT dataset;
the first and second planes are non-parallel acquisition planes.

10. A method in accordance with claim 1, wherein:
a field of view of the second image is at least initially constrained to correspond with a field of view of the first image.

11. A method in accordance with claim 1, wherein:
a field of view of the second image is at least initially constrained to correspond with a field of view of the first image; and
a field of view of the fourth image is at least initially constrained to correspond with a field of view of the third image.

12. A method in accordance with claim 1, wherein:
the second dataset is a 3-D multi-volume medical scan dataset;
the second image is obtained from a first volume of the second dataset, the first volume of the second dataset including the same part of the scanned object as the first volume of the first dataset; and
the fourth image is obtained from a second volume of the second dataset, the second volume of the second dataset including the same part of the scanned object as the second volume of the first dataset.

13. A method in accordance with claim 1, wherein:
the first plane is a curved cut of the first dataset.

14. A hybrid medical imaging scanner, comprising:
a medical imaging workstation arranged to control a scanning unit to obtain a first medical scan dataset and a second medical scan dataset,
the first medical scan dataset resulting from a scan of a 3-dimensional (3-D) object with a first scanning mode, the first scanning modality being one of, or a combination of: Magnetic Resonance Imaging (MRI); Computed Tomography (CT); Positron Emission Tomography (PET); X-Ray; Ultrasound (US); and Single Photon Emission Tomography (SPECT);

the second medical scan resulting from a scan of the object with a second scanning mode, the second scanning modality being one of, or a combination of: MRI; CT; PET; X-Ray; US; and SPECT;

the first and second medical scan datasets are 3-dimensional (3-D) datasets; and at least the first medical scan dataset is a multi-volume dataset, comprising at least a first volume of the 3-D object and a second volume of the 3-D object obtained by scanning the 3-D object in a single sitting of the first scanning modality; and where the medical imaging workstation is further adapted to perform the steps of:

deriving a first image from the first medical scan dataset, the first image lying in a first plane, the first plane corresponding to an acquisition plane of the first medical scan dataset, the acquisition plane being an imaging plane used at the time of acquisition of the first volume of the first medical scan dataset; and obtaining a second image, from the second medical scan dataset, the second image lying in the first plane; and a display, for displaying the first image and the second image simultaneously, wherein the medical imaging workstation is further adapted to performs the steps of, upon a user selecting to switch to a view of an image from the second volume of the first medical scan dataset:

deriving a third image from the second volume of the first medical scan dataset, the third image lying in a second plane, the second plane corresponding to an acquisition plane of the second volume;

obtaining a fourth image from the second medical scan dataset, the fourth image lying in the second plane; and displaying the third image and the fourth image simultaneously.

15. A hybrid medical imaging scanner in accordance with claim 14, further comprising user interface means, the user interface means performing the step of:

presenting a user with at least the following options for image display orientation: axial; coronal; sagittal; acquisition; and when a user selects the acquisition option, causing the display of the first image and the second image in the plane in which the first image was acquired.

16. A method of creating and simultaneously displaying medical scan images, from each of:

(i) a first multi-volume medical scan dataset, obtained by scanning a 3-dimensional (3-D) structure with a first scanning modality, wherein:

the first scanning modality is one of, or a combination of: Magnetic Resonance Imaging (MRI); Computed Tomography (CT); Positron Emission Tomography (PET); X-Ray; Ultrasound (US); and Single Photon Emission Tomography (SPECT), and the first multi-volume medical scan dataset comprises at least a first volume of the 3-D structure and a second volume of the 3-D structure obtained by scanning the 3-D structure in a single sitting of the first scanning modality; and (ii) a second medical scan dataset, obtained by scanning the 3-dimensional (3-D) structure with a second scanning modality, the second scanning modality being one of, or a combination of: MRI; CT; PET; X-Ray; US; and SPECT;

the first and second medical scan datasets being 3-dimensional (3-D) datasets;

the method comprising:

displaying a first image derived from the first volume of the first medical scan dataset, an extent of the first image comprising a field of view derived from the first volume of the first medical scan dataset;

wherein the first image lies in a first plane, the first plane corresponding to an acquisition plane of the first volume of the first medical scan dataset, the acquisition plane being an imaging plane used at the time of acquisition of the first volume of the first medical scan dataset;

displaying a second image, obtained from the second medical scan dataset, together with the first image, an extent of the second image being locked to the field of view, the method further comprising, upon a user selecting to switch to a view of an image from the second volume of the first medical scan dataset:

displaying a third image derived from the second volume of the first medical scan dataset, an extent of the third image comprising a field of view derived from the second volume of the first medical scan dataset;

displaying a fourth image, obtained from the second medical scan dataset, together with the third image, an extent of the fourth image being locked to the field of view of the third image; and displaying the third image and the fourth image simultaneously.

* * * * *